United States Patent [19]

Mussmann et al.

[11] Patent Number: 4,682,157

[45] Date of Patent: Jul. 21, 1987

[54] POLAR FLUID DETECTION SYSTEM UNAFFECTED BY POWER LINE VOLTAGES

[75] Inventors: Sara M. Mussmann, Indianapolis; Roy E. Kidd, Clayton, both of Ind.

[73] Assignee: Emhart Industries, Inc., Indianapolis, Ind.

[21] Appl. No.: 833,188

[22] Filed: Feb. 27, 1986

[51] Int. Cl.⁴ ............... G08B 21/00; H03K 5/153; H01H 47/12

[52] U.S. Cl. .................. 340/605; 340/620; 328/4; 307/308; 307/360; 361/178

[58] Field of Search ............ 340/603, 618, 605, 620; 328/1, 4; 307/308, 360; 328/162, 165; 361/178

[56] References Cited

U.S. PATENT DOCUMENTS 4,586,033  4/1986  Andrejasich .............. 340/603

Primary Examiner—Stanley D. Millen
Assistant Examiner—Trong Quang Phan
Attorney, Agent, or Firm—Robert F. Meyer; Carl A. Forest

[57] ABSTRACT

A detector for sensing the presence of polar fluids includes a pair of detection probes and a circuit for providing an oscillating voltage across the probes. A power supply for the detector includes a transformer with a split secondary, with at least one secondary having a floating ground. One of the probes is connected to the floating ground. The other probe is connected to the input of a fluid detection logic circuit. The input is applied to an inverter having an activation threshold of approximately six volts. The resulting activation threshold of the detector circuit is sufficiently low to be activated by the oscillating voltage so as to produce a polar fluid output signal when the probes are immersed in a polar fluid, but sufficiently high so as not to be affected by stray voltages induced in the probes by conventional power lines, such as 120 VAC lines, contacting the polar fluid.

6 Claims, 2 Drawing Figures

FIG. 1

POLAR FLUID DETECTION SYSTEM UNAFFECTED BY POWER LINE VOLTAGES

BACKGROUND OF THE INVENTION

1. Field of the Invention

The invention in general relates to fluid detectors that can sense the difference between polar and non-polar fluids, and in particular to such a detector which remains accurate when conventional electric power lines come into contact with the polar fluid it is sensing.

2. Description of the Prior Art

The contamination of ground water by pollutants has become a problem in recent years. One type of such contamination occurs when storage tanks containing hydrocarbons, such as gasoline or oil, leak. Since many underground storage tanks that were installed during a "gas station boom" that occurred many years ago are now beginning to leak, and the cleanup of leaks that go undetected can easily run into millions of dollars, the detection of such leaks has become very important. Hydrocarbons, such as gasoline are non-polar fluids, while ground water is a polar fluid, and thus detectors that can sense the difference between polar and non-polar fluids have become a common means for detecting such gasoline leaks.

One type of detector that has been developed to detect hydrocarbon pollutants in ground water is one that employs two conductive probe members to which an oscillating voltage is applied. These detectors sense the differing conductivity of ground water and hydrocarbons to produce signals indicating which of the two fluids are present. See, for example, U.S. patent application Ser. No. 06/579,431, (now U.S. Pat. No. 4,586,033).

A problem that can occur with such detectors is that voltages and currents in the ground water in which the probe members are immersed can affect the measurements of the device and cause hydrocarbon alarms when no hydrocarbon is present. This problem has been found to occur with surprising frequency in areas, such as Florida, where the ground water levels are high. It has been found that the high ground water levels often result in the water coming in contact with power lines. ("Power Line" herein is defined as a conventional power line, such as those carrying 120 VAC, which generally carry power on the order of a hundred volts or greater.) Since areas with high water levels are also generally areas where underground tanks corrode and leak much more rapidly, it would be highly desirable to provide a detector which was not affected by the power lines coming in contact with the ground water.

The prior art detectors also have the problem that there is a large variation in resistance threshold, i.e. the probe resistance which causes a change in signal, from device to device. This requires careful resistance matching during manufacture which is highly labor-intensive and thus costly.

SUMMARY OF THE INVENTION

It is an object of the invention to provide a detector for sensing the presence of polar fluids and which is not affected by the electric currents and voltages in the polar fluid which result when power lines come into contact with the fluid.

It is another object of the invention to provide a polar-non-polar fluid detector in which the detector circuitry has a higher activation threshold than the prior art hydrocarbon detectors.

It is a further object of the invention to provide a polar-non-polar fluid detector in which the activation threshold floats in the presence of electric voltages and currents caused by power lines coming into contact with the polar fluid which is being detected.

The invention provides an apparatus for sensing the presence of polar fluids, comprising: probe means; means for providing an oscillating voltage to the probe means; detector means for providing a fluid polar characteristic related signal, the detector means including a means for preventing voltages in said polar fluid caused by power lines coming into contact with said fluid from altering said signal. Preferably the means for preventing includes a means for allowing the ground of said detector means to float. Preferably the means for allowing the ground to float includes a power transformer having two secondary windings, one winding being connected to said detector means and having a floating ground. Preferably, the means for preventing includes a digital gate having an input threshold of four volts or higher. The detector according to the invention not only provides accurate readings in the presence of external voltages, but also is less expensive to manufacture than the prior art detectors and has a stable resistance threshold from device to device. Numerous other features, objects and advantages of the invention will become apparent from the following detailed description when read in conjunction with the accompanying drawings.

BRIEF DESCRIPTION OF THE DRAWINGS

In the drawings

FIG. 1 is a diagramatic illustration of a detector-probe assembly according to the invention including a detailed electrical circuit diagram of the assembly.

DESCRIPTION OF THE PREFERRED EMBODIMENT

Figure 1:
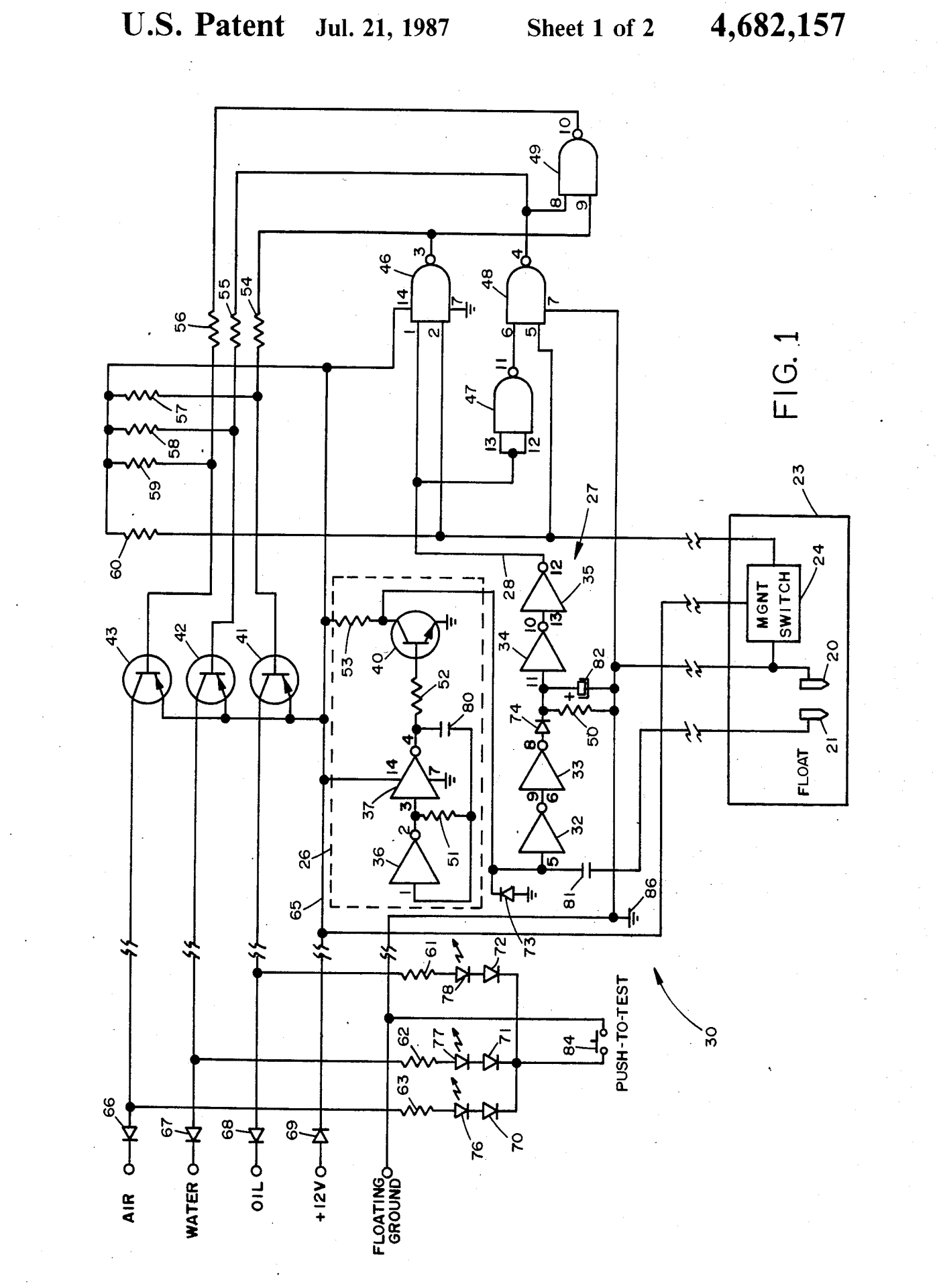
Figure 2:
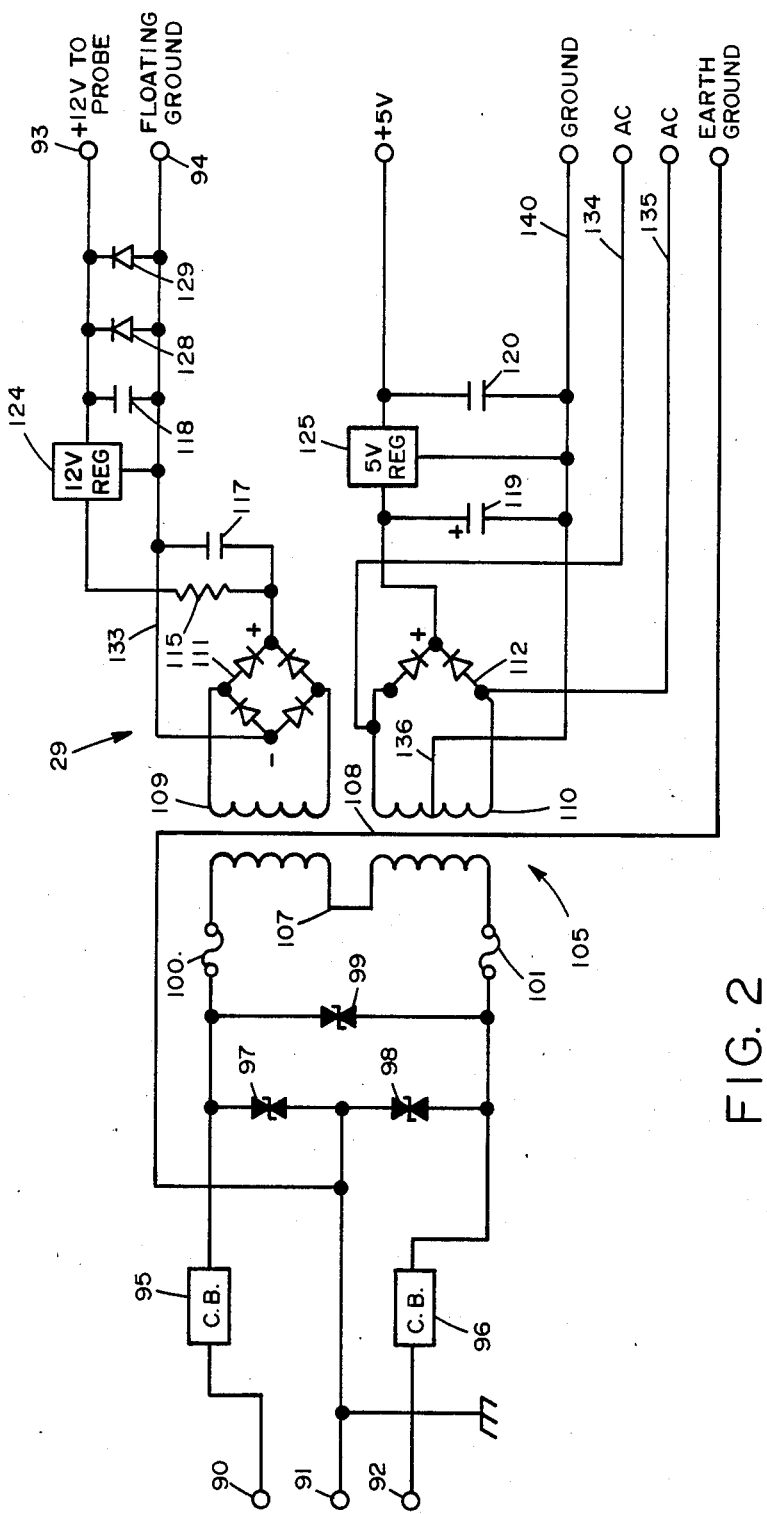
FIG. 2 is a detailed circuit diagram of the power supply for the detector-probe assembly of FIG. 1.

The preferred embodiment of a detector-probe assembly according to the invention is shown in FIG. 1. The assembly includes probes 20 and 21 which may be mounted on a float 23 as is common for water/hydrocarbon detectors. There is a circuit means 26 (generally, the circuit enclosed by the dotted line) for providing an oscillating (or A.C.) signal to the probes 20 and 21. The detector means 27 for providing a fluid polar characteristic signal (on line 28) is generally located in the middle of FIG. 1 below oscillator 26, though it also includes the floating ground circuitry 29 in FIG. 2. This detector means 27 includes means 30 including inverters 32 through 35 and floating ground circuitry 29 for preventing voltages in the polar fluid from altering the fluid polar characteristic signal on line 28.

Turning to a more detailed description of the preferred embodiment of the invention, the detector-probe assembly of FIG. 1 includes probes 20 and 21, magnetic switch 24, inverters 32 through 37, transistors 40 through 43, NAND gates 46 through 49, resistors 50 through 63, diodes 66 through 74, light-emitting diodes (LED's) 76, 77 and 78, capacitors 80, 81, and 82, and switch 84. The floating ground is indicated by the common ground symbol as at 86. The numbers on the inputs and outputs of the gates (inverters and NAND gates) such as the 1 on the input to inverter gate 36, indicate the pin number of the IC's of which these devices are part (see below).

The circuit composed of inverters 36 and 37, resistor 51, and capacitor 80 is an approximately 670 Hertz oscillator. The output of inverter 37 is applied to its input through capacitor 80 and resistor 51. The line between capacitor 80 and resistor 51 is also connected to the input of inverter 36. The output of inverter 36 is connected to the input of inverter 37. The No. 14 pin of the inverter 37 is connected to the 12 volt power line 65, while the No. 7 pin is connected to circuit ground. The output of inverter 37 is also connected to the base of transistor 40 through resistor 52. The emitter of transistor 40 is connected to the floating ground. The collector is connected to the +12 V power supply line 65 through resistor 53.

The collector of transistor 40 is also connected to ground through diode 73, with the anode of diode toward the ground, to probe 21 through capacitor 81, and to the input of inverter gate 32. The output of inverter 32 is connected to the input of inverter 33 and the output of inverter 33 is connected to the anode of diode 74. The cathode of diode 74 is connected to the input of inverter 34 and to probe 20 through resistor 50 and capacitor 82 in parallel. Probe 20 is also connected to the floating ground. The output of inverter 34 is connected to the input of inverter 35 and the output of inverter 35 is connected to one input of NAND gate 46 and both inputs of NAND gate 47.

One side of magnetic switch 24 is connected to ground and the other side is connected to the other input of NAND gate 46, to one input of NAND gate 48, and to the +12 volt power line 65 through resistor 60. The power input to magnetic switch 24 is connected to the power line 65. The output of NAND gate 47 is connected to the other input of gate 48. The output of NAND gate 46 is connected to one input of NAND gate 49 and to the base of transistor 41 through resistor 54. The output of NAND gate 48 is connected to the other input to NAND gate 49 and to the base of transistor 42 through resistor 55. The output of NAND gate 49 is connected to the base of transistor 43 through resistor 56. The bases of transistors 41, 42 and 43 are also each connected to the power line 65 through resistors 57, 58 and 59, respectively.

The emitters of transistors 41, 42 and 43 are connected to the power line 65. The collectors of each of transistors 41, 42 and 43 are connected to the anode of LED's 78, 77 and 76, respectively through resistors 61, 62 and 63, respectively. The cathode of each of LED's 76, 77 and 78 are connected to the anodes of diodes 70, 71 and 72, respectively. The cathode of diodes 70, 71 and 72 are each connected to one side of switch 84. The other side of switch 84 is connected to the floating ground. The collector of transistors 43, 42 and 41 are also connected to the "AIR", "WATER" and "OIL" outputs respectively through diodes 66, 67 and 68, respectively, with the anodes of the diodes toward the transistors. The "AIR", "WATER" and "OIL" outputs connect to a central station (not shown) which monitors the outputs of many detector-probe assemblies, such as the one just described, at different remote locations. The power line 65 is connected to the +12 V power input through diode 69 with the anode of the diode toward the input. The +12 V power input and the floating ground are connected to the respective outputs of the power supply of the central station, which power supply is shown in FIG. 2.

Turning now to FIG. 2, the power supply, which would generally be located in the central station which controls and monitors a number of detector-probe assemblies is shown. Input terminals 90, 91 and 92 are connected to a conventional three-pronged plug, with terminal 91 being the earth ground. Output terminals 93 and 94 connect to the +12 V power input and floating ground respectively of the detector-probe assemblies.

The components of the preferred embodiment of the power supply comprises circuit breakers 95 and 96, varistors 97, 98 and 99, fuses 100 and 101, transformer 105, bridge rectifiers 111 and 112, resistor 115, capacitors 117, 118, 119 and 120, voltage regulators 124 and 125, and diodes 128 and 129. One side of the primary coil 107 of transformer 105 is connected to input 90 through fuse 100 and circuit breaker 95. The other side of primary 107 is connected to input 92 through fuse 101 and circuit breaker 96. The transformer core 108 and the earth ground output for the central station (not shown) electronics is connected to terminal 91. Varistors 97 and 98 are connected between terminal 91 and the lines between circuit breakers and fuses 95 and 100 and 96 and 101 respectively, and varistor 99 is connected between the same two lines. Transformer 105 has a split secondary comprising coils 109 and 110. Coil 109 is connected across the input terminals of bridge rectifier 111 while coil 110 is connected across the input terminals of bridge rectifier 112.

The negative output terminal of rectifier 111 is connected to the floating ground line 133 while the positive terminal is connected to the input of voltage regulator 124 through resistor 115 and also to the ground line 133 through capacitor 117. The output of voltage regulator 124 is connected to the +12 V output and the regulator ground is connected to ground line 133. Capacitor 118 and diodes 128 and 129 are connected in parallel between the +12 V output line and the floating ground line 133 with the anodes of the diodes toward the ground.

The AC power lines 134 and 135 which provide AC power to the central station are also connected to either side of secondary 110. Center tap 136 of secondary 110 is connected to the 5 V power supply ground line 140. The positive output of bridge rectifier 112 is connected to the input of voltage regulator 125. The input of voltage regulator 125 is also connected to ground line 140 through capacitor 119. The ground terminal of voltage regulator 125 is connected to ground line 140. The output of voltage regulator 125 provides the +5 V power for the central station. Capacitor 120 is connected between the +5 V line and ground line 140.

In the preferred embodiment of the invention, the parts are as follows: probes 20 and 21 are pointed rods made of a conductive material resistant to corrosion, such as stainless steel or platinum. The rods are threaded for mounting and adjusting on the float 23. Magnetic switch 24 is either a reed switch or a Hall Effect switch. (The connection of the switch 24 to the power line 65 is only necessary in the case of the Hall Effect switch.) Inverters 32 through 37 are a six-inverter package type 4069. Transistor 40 is a PN 2222 and transistors 41 through 43 are PN2907's.

Gates 46 through 49 are a four-gate IC package type 4011. Resistors 50, 51, 52 and 53 are 100K ohm, 220K ohm, 100K ohm, and 150K ohm, respectively, resistors 54, 55 and 56 are each 10K ohm, resistors 57 through 60 are 100K ohm, and resistors 61, 62 and 63 are 820 ohm. Capacitor 80 is a 0.0047 microfarad, 81 is a 0.1 microfarad capacitor, and 82 is a 1 microfarad capacitor. Diodes 66 through 69 and 73 are IN4001's, and 70, 71, and 72 and 74 are IN914's. LED's 76 through 78 are green, yellow, and red LED's respectively. Turning to FIG. 2 and continuing: circuit breakers 95 and 96 are 1 amp rated, fuses 100 and 101 are 0.175 amp, varistors 97 through 99 are type V150 metal oxide varistors, transformer 105 is made by Cramer, Inc. of Grafton, Wis. and includes a 12 volt transformer (secondary 109) and a 24 volt transformer (secondary 110) with a center tap and having the core grounded for intrinsic safety. Bridge rectifiers 111 and 112 are type FW100 (1 AMP). (Only one half of rectifier 112 is shown as only half is used.) Resistor 115 is 10 ohm, capacitors 117 and 119 are 1000 microfarads, and 118 and 120 are 0.1 microfarads. Voltage regulator 124 is an LM140K-12 and 125 is an LM140K-5. Diodes 128 and 129 are IN5352's.

The invention operates in the following manner. As mentioned above, the inverters 36 and 37 and their associated circuitry provide a 670 Hertz signal at the output (pin 4) of inverter 37. Transistor 40 isolates the oscillator from the rest of the circuitry and inverts the oscillating signal. The signal is passed to probe 21 through isolation capacitor 81. Diode 73 passes any negative going current induced on the probes to ground. Gate 32 requires from about 4 to 9 volts to trigger its output from a high to low state; this relatively high voltage compared to the prior art prevents positive going induced current from affecting the detector output. If the probes are in a non-polar fluid, such as air or hydrocarbon, on the high part of the oscillation inverter 32 goes low, inverter 33 goes high, inverter 34 goes low, and inverter 35 goes high to produce a high signal on line 28. The capacitor 82 will discharge the high signal at the input to inverter 34 if the high in the output of inverter 33 is not refreshed. So long as the probes are in a non-polar fluid, the high is refreshed about 670 times a second. Resistor 50 determines the time constant for discharge of capacitor 82. Diode 74 prevents the capacitor 82 from discharging to the low on the output of inverter 33 during the low part of the oscillation.

If the probes are immersed in a polar fluid, such as ground water, there is essentially a short across the probes and the ground of probe 20 pulls probe 21 and the input of inverter 32 low, which produces a low signal on line 28.

The magnetic switch 24 is activated by a magnet (not shown) at the bottom of float movement to provide a second bit of data which differentiates between the two non-polar fluids, air and hydrocarbon. If the probe well is dry, the output of magnetic switch 24 is low, and if the probe well contains liquid the output will be high.

The gates 46 through 49 provide a logic network which determines the status of the probes from the signal on lines 28 and the output of the magnetic switch. If the well is dry, the number 1 pin of gate 46 is high and the number 2 pin is low producing a high signal at the output of gate 46. Both inputs to gate 47 will be high, and its output will be low. Both inputs to gate 48 will thus be low and its output will be high. Thus both inputs to gate 49 will be high and its output will be low. The low on the gate of transistor 43 will turn it on which will provide a high signal on the "AIR" output and cause LED 76 to light when switch 84 is closed. Likewise, the other combinations of data input signals will produce a high signal on the "WATER" output when the probes are in water and a high signal at the "OIL" LED's when the monitoring elements are in hydrocarbon respectively when switch 84 is closed. Diodes 66 through 69 provide reverse bias protection and resistors 54 through 60 limit the current. Likewise diodes 70, 71 and 72 provide isolation protection and resistors 61, 62, 63 provide the current-limiting effect for their respective LED's.

Turning to FIG. 2, any induced voltage on both the probes 20 and 21 will have no affect on the operation of the circuit connected to secondary 109 since the operation of all the elements of this current depend only on the relative voltage difference between the positive voltage line and the floating ground. Since the probes are relatively close physically, there generally will be little difference between them with respect to the effect of ground currents. What difference there is is handled as discussed above by diode 73 and inverter 32 and the associated detector circuitry.

The circuit according to the invention can handle much greater induced probe voltages than the prior art circuits without providing inaccurate readings. In the prior art circuits, induced voltages of from 0.4 to 0.8 volts could cause the output indication to change to "OIL" even though the probes were still immersed in water. In the circuit according to the invention, it took induced voltages of from 17.9 to 24.6 volts to affect the output under the same conditions. Thus the detector according to the invention is much less sensitive to voltages and currents induced in the probes 20 and 21 by electric power lines coming in contact with the polar fluid being sensed.

The circuit according to the invention provides for a lower frequency of oscillation than the prior art polar-non-polar fluid detection circuits. This permits a higher capacitance threshold between the probes to produce a water output, which further contributes to the reliability and stability of the system.

Another feature of the invention is that the inverter gates employed in the detection circuit have much higher reproducability of the gate threshold as compared to the transistors which determined the threshold in the prior art. This results in a more consistent resistance threshold from device to device which allows one to eliminate the resistance matching that was required in the prior art circuits.

In addition, the circuit of the present invention is simpler than the circuits of the prior art, and the components of the detector circuit such as the inverter 32 through 37, are less expensive than the prior art components.

A novel fluid detection system which operates accurately and reproducibly in the presence of induced currents and voltages caused by power lines coming in contact with a polar fluid being sensed has been described. Although the invention has been disclosed with respect to a particular embodiment, it is understood that numerous other embodiments may be devised. Further, it is evident that those skilled in the art may now make many uses and modifications of the embodiment described without departing from the inventive concepts. For example, other equivalent electronic parts may be used. The probe circuitry may be placed in many different packages, with or without a float or magnetic switch. Consequently, the invention is to be construed as embracing each and every novel feature and novel combination of features present in the fluid detector described.

What is claimed is:

1. An apparatus for sensing the presence of polar fluids regardless of the presence of undesired power line voltages comprising:
   probe means for contacting said polar fluid;
   means for providing an oscillating voltage to said probe means,
   detector means for providing a fluid polar characteristic related signal, said detector means electrically connected to said probe means for sensing the state of said probe means and including a means for preventing said undesired voltages in said polar fluid caused by said electric power lines coming in contact with the fluid from altering said signal and adversely affecting said detector means.

2. The apparatus of claim 1 wherein said means for preventing voltages comprises a digital gate having an input threshold of the level of 4 volts or greater.

3. The apparatus of claim 2 wherein said digital gate comprises an inverter.

4. The apparatus of claim 1 wherein said means for preventing voltages comprises a means for allowing the ground voltage level of said detector means to float.

5. The apparatus of claim 4 wherein said means for allowing the ground voltages level of said detector means to float comprises a power transformer having two secondary windings, one winding electrically connected to said detector means and having a floating ground.

6. An apparatus for sensing the presence of polar fluids regardless of the presence of undesired power line voltages comprising:
   probe means for contacting said polar fluid;
   means for providing an oscillating electrical voltage to said probe means;
   means for providing a fluid polar characteristic related signal, said means for providing including an electrical gate means having a threshold input connected to said probe means, said threshold input having a threshold voltage level sufficiently high that said electrical gate means is not activated by said undesired voltages induced in said probe means by said electric power lines contacting the polar fluid to be sensed, but sufficiently low to be activated by said oscillating electrical voltage.

* * * * *